United States Patent
Zecchino et al.

(12) 
(10) Patent No.: US 6,497,887 B1
(45) Date of Patent: Dec. 24, 2002

(54) MEMBRANE DELIVERY SYSTEM

(75) Inventors: Jules Zecchino, Closter, NJ (US); E. Althea Knight, Teaneck, NJ (US); Carmen Castillo-Bucci, Greenlawn, NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/549,113

(22) Filed: Apr. 13, 2000

(51) Int. Cl.[7] .............................. A61K 7/00; A61K 7/48
(52) U.S. Cl. .................... 424/401; 424/427; 424/78; 424/451; 604/20
(58) Field of Search ....................... 424/427, 78, 451; 604/20; 602/49

(56) References Cited

U.S. PATENT DOCUMENTS

| | | | | |
|---|---|---|---|---|
| 4,188,373 A | * | 2/1980 | Krezanoski | 424/78 |
| 4,651,725 A | * | 3/1987 | Kifune et al. | 602/49 |
| 5,318,780 A | * | 6/1994 | Viegas et al. | 424/427 |
| 5,328,455 A | * | 7/1994 | Iiyod et al. | 604/20 |
| 5,405,616 A | * | 4/1995 | Wunderlich et al. | 424/451 |
| 5,456,745 A | | 10/1995 | Roreger et al. | 106/128 |
| 5,541,234 A | * | 7/1996 | Unger et al. | 521/66 |
| 5,785,978 A | | 7/1998 | Porter et al. | |
| 5,939,485 A | | 8/1999 | Bromberg et al. | 524/556 |
| 5,989,557 A | * | 11/1999 | Bombardelli et al. | 424/195.1 |

FOREIGN PATENT DOCUMENTS

| | | | |
|---|---|---|---|
| WO | 93/11803 | 6/1993 | A61L/15/28 |
| WO | 97/02845 | 1/1997 | A61L/15/28 |

* cited by examiner

*Primary Examiner*—Jose' G. Dees
*Assistant Examiner*—M. Haghighatian
(74) *Attorney, Agent, or Firm*—Karen A. Lowney, Esq.

(57) ABSTRACT

The present invention relates to a delivery system for topical application to the skin comprising a freeze-dried, partially cross-linked polymeric gel membrane which can be reversibly returned to a dissolvable gel form upon the application of a wetting agent. The membrane can be used to deliver biologically active agents to the skin.

26 Claims, No Drawings

MEMBRANE DELIVERY SYSTEM

FIELD OF THE INVENTION

The present invention relates to a delivery system for application to the skin. In particular, the invention relates to a membrane-based system useful in delivering biologically active materials to the skin.

BACKGROUND OF THE INVENTION

The problem of effective delivery of active ingredients to the desired target site is one which continues to be problematic for both the cosmetic and pharmaceutical industries. Topical delivery of active agents is particularly difficult because, unlike parenteral or oral delivery, while the skin is certainly readily accessible, the exposure of the site at which the product is delivered can work against the goal of fully efficient receipt of the active by the target area. Typical vehicles for topical applications have normally been lotions, creams and gels, relatively viscous fluids that are rubbed into the skin, providing immediate contact with the target region. These vehicles are frequently very successfully used for active delivery, both of cosmetic and pharmaceutical delivery. They are, however, without more, not capable of delivering the active therein over long periods of time, which is sometimes required for the greatest efficacy of the active. In addition, from a strictly practical point of view, they are not frequently very portable, so that the user is frequently required to carry a bulky jar or bottle if the product is to be used outside the home.

Dermal patches represent an alternative to the liquid forms of application. These devices can come in a variety of forms, all having the capability of adhering to the skin, and thereby permitting prolonged contact between the active-containing composition and the target area, They also have the advantage of being relatively compact and portable, and permitting very precise delivery of product to the area to be treated. These patches come in a variety of forms, some containing fluid reservoirs for the active component, others containing dry ingredients that are released upon contact with moisture in the skin. Many require some form of adhesive to retain them in connection with the skin for an adequate period. A different type of patch is applied dry, with water applied to wet the patch to form a sticky film that is retained on the skin. Such films normally need to be washed or peeled off the skin, and can be very visible; for this reason they can be aesthetically unpleasant.

There thus continues to be a need for a topical delivery system which will be more convenient to use and more elegant than previous delivery forms and devices, while at the same time retaining the efficiency of providing the desired actives to the target location. The present invention now provides such a system.

SUMMARY OF THE INVENTION

The invention provides a delivery system for topical application to the skin comprising a freeze-dried, partially cross-inked polymeric gel membrane which can be reversibly returned to a dissolvable gel form upon the application of a wetting agent. In a preferred embodiment, the membrane also incorporates biologically active agents for delivery to the skin. Unlike previous "patches" or similar spot treatments, that need to washed or peeled off, the membrane of the present invention, when wet, assumes its previous gel form, which can be readily rubbed into the skin, thereby delivering the active agents and leaving substantially no residue to be removed from the application area. An additional benefit is that the membrane also stabilizes the actives contained therein, thereby allowing for prolonged storage and shelf-life of otherwise potentially unstable active materials.

DETAILED DESCRIPTION OF THE INVENTION

The membranes of the invention are based on a partially cross-linked gel network of polymeric material having sufficient structure to permit the suspension of one or more actives and to survive a freeze-drying process, but the structure of which is also reversible, so as to subsequently allow the return of the membrane to the gel condition when water or other wetting agent is applied. The reversibility of the structure allows the user to then rub the gel film into the skin, thereby avoiding the necessity of rinsing or peeling off a dried film, as is required with other types of skin patches.

A number of different types of polymers can be used as the base of the membrane. The polymers employed must of course be sufficiently water soluble to respond to the aqueous wetting agent that will eventually be applied. Preferred polymers are those which produce a fibrous type of gel network when cross-linked, the strength of the fibers being adequate to withstand the freeze-drying process, but as noted, adequately water-soluble to permit rewetting. Particularly preferred are gels based on alginic acid, for example, i.e., sodium or calcium alginate gels. However, other types of cross-linkable gel-forming polymers can also be used; examples of alternate bases for the gel include collagen, particularly partially hydrolyzed collagen, or cross-linkable starches.

The membrane is formed by standard methods of crosslinking of the chosen gel-forming polymer. For example, if the chosen gel is an alginate, this is normally achieved by the addition of a solution containing metal ions to a slurry of the alginate and water. Examples of useful sources of such metal ions include, but are not limited to, strongly electrolytic cosmetically or pharmaceutically acceptable acid salts of mono-, or more preferably, di- or trivalent metals, such as $K^+$, $Ca^{+2}$, $Al^{+2}$, $Fe^{+2}$, $Fe^{+3}$, $Cu^{+2}$, or $Mn^{+2}$. The relative proportions of the components in the slurry are not very critical; however, for the wet gel, the polymer will normally constitute from about 0.5 to about 10% by weight; and the metal salts normally will be added in an amount of about 0.5 to about 3%. The amount of the polymer relative to the remaining dry ingredients to be included in the membrane will normally be from about 30 to about 70% by weight, preferably from about 45 to about 55% by weight of the dried composition. Gels based on other polymers are similarly prepared in accordance with known techniques. For example, if collagen is the chosen base for the gel, the cross-linking agent is normally an aldehyde, and with starch, a large number of crosslinking agents, such as phosphorus oxychloride, or epichlorohydrin, are also useful. In all cases, to this point, the procedure of gel formation is a routine preparation of the chosen type of gel.

However, for the purposes of the present membrane, it is desirable to interfere somewhat with the cross-linking, but only partially, so as to form an adequately supportive network, but to also permit reversal of the structure of the matrix back to its original gel state on contact with water. To achieve this, a cross-linking disrupter is added to the slurry of metal ions and polymer. In general terms, the disrupter is a hygroscopic material, and preferably of a fairly high molecular weight. The size of the molecule aids in the interference with cross-linking, while the hygroscopic property aids in the ultimate rewetting of the membrane at the appropriate time. Examples of materials of this type include breakdown products and derivatives of chitin and mucopolysaccharides, for example, chitosan, hyaluronic acid, glucuronic acid, and oligosaccharides(natural or synthetic) comprising glucosamine, galactosamine, and/or mannosamine monomeric units; hygroscopic, water soluble amino acids or peptides composed thereof, for example, glycine or lysine, or glycerin and glycerin derivatives. A particularly preferred cross-linking disrupter is hyaluronic acid . The disrupter is used in an amount sufficient to constitute from about 0.01 to about 10%, preferably about 1 to about 8%, by weight of the dried membrane.

Although the gel formed by the crosslinked polymer forms an adequate film to retain the product on the skin at the time of wetting, it may also be desirable to add small amounts of additional film-forming agents to the membrane mixture. Such film-forming agents should also be water soluble, and should be used in such amounts so as to not interfere with the dissolvability of the membrane on the skin. Examples of useful film-forming agents for this purpose include, but are not limited to, collagen derivatives, cellulose derivatives, e.g., carboxymethylcellulose, hydroxymethylcellulose, hydroxypropylcellulose, homo- and copolymers of vinyl pyrrolidone, e.g., PVP, or PVP/PVA copolymers; homo-or copolymers of vinyl alcohol, such as polyvinyl alcohol, homo- or copolymers of acrylic and/or methacrylic acids, and salts and esters thereof, or gums, e.g., xanthan gum, guar gum, alginates, or carrageenan. If used, the additional film-former will be used in an amount of about 0.001% to about 25% by weight of the dry membrane, preferably about 0.1 to about 20%. It may also be desired, but not essential, to use small amounts of fibrous material, such as rayon, to supplement the structure of the membrane while freeze drying. If used at all, the amount is preferably less than about 10%, more preferably less than 5%.

The membrane is made by first preparing a slurry of the chosen polymer in water, and then adding the disrupter, as well as any additional materials, such as film forming agents and actives. The aqueous solution containing the requisite crosslinking agent is then added to the slurry, thereby setting up, by virtue of the presence of the disrupter, a partially crosslinked matrix. The solid matrix is then freeze-dried, under known and standard conditions, to remove any water thereby forming a dry film or block. The dried film or block is then sliced or otherwise divided or cut to prepare application pieces of the desired size and shapes, with a thickness generally of about 0.1 mm to about 1.5 mm, preferably, from about 0.2 mm to about 1 mm, and more preferably about 0.2 mm to about 0.6 mm. The final thickness will be a matter of choice dependent upon the intended use. The shapes of the application pieces can also be varied in accordance with their intended end use, and can be as large or as small as required for the purpose.

In order to function on the skin, the membrane must be rewetted with a wetting solution or activator. The wetting solution may be as simple as ordinary water, depending on the relative water solubility of the polymer used in preparation of the matrix and the nature of the additional components in the membrane. However, it is preferred that the wetting solution be slightly acidic, i.e., having a pH of between about 2 to about 6, preferably about 4 to about 6, in order to facilitate dissolution of the matrix. Thus, any aqueous solution containing a cosmetically or pharmaceutically acceptable acid will be appropriate for use in rewetting. However, in one embodiment of the invention, it particularly preferred that the wetting solution contain at least one alpha or beta hydroxy acid as the acid component. As is well documented, these acids themselves have a beneficial effect on the skin, as well as being able to enhance the rewetting of the membrane. Examples of useful acids for this purpose include, but are not limited to, lactic acid, glycolic acid, citric acid, alpha-hydroxyoctanoic acid, alpha-hydroxydecanoic acid, alpha-hydroxylauric acid, tartaric acid, glucouronic acid, galactouronic acid, acrylic acid, alpha-hydroxybutyric acid, alpha-hydroxyisobutyric acid, malic acid, mandelic acid, phosphoric acid, pyruvic acid, tartronic acid, lactobionic acid and salicylic acid. The acid is preferably used in a concentration of about 0.01 to about 20% by weight of the wetting solution. In an alternate embodiment, for example, in a case in which the membrane contains an acidic active, it may be desirable to incorporate a bicarbonate into the solution, so that the reaction between the bicarbonate and the acid creates an additional force for dissolution of the membrane. In such a case, the wetting solution will ordinarily contain little or no acid, so as to avoid a premature reaction of acid and bicarbonate. The bicarbonate will ordinarily be sodium or potassium bicarbonate, present in an amount of about 0.1 to about 10% by weight of the solution. In a reversal of this process, the bicarbonate can alternately be incorporated into the membrane, and then will react with an acidic wetting solution. Again, in such a case, care must be taken so as to avoid a premature reaction with acid; therefore, if the membrane contains an acidic active, the bicarbonate can be sprinkled upon the dried membrane, and then activated by exposure to the wetting solution, which can be either ordinary or acidic water.

Either the membrane or the wetting solution can also contain additional optional cosmetic ingredients that contribute to the aesthetics of the system. For example, either component of the system may contain cosmetic oils, particularly silicone oils or esters, to enhance the emolliency of the gel in use on the skin. In fact, the wetting solution itself may be a water and oil emulsion or biliquid foam, rather than a simple aqueous solution. Either portion of the system may also comprise optical diff-users (soft focus powders), and/or silicone polymers, which will aid in softening the appearance of the membrane on the skin. Perfluoroethers can also be employed to assist in preventing feathering in areas prone to this occurrence, such as the upper lip. It is also possible to incorporate active components into the wetting agent. Other possible components will be readily apparent to those skilled in the art, given the understanding that the additional components cannot interfere with the integrity of the membrane upon drying, or with the ability of the wetting agent to dissolve the gel membrane.

As noted above, the wetting of the membrane can be achieved with ordinary water, so that the membrane can stand alone as the delivery system. However, in a preferred embodiment of the invention, a specially adapted wetting solution, as described above, and the membrane application pieces are packaged and purchased together in kit form. The use of the delivery system is very simple. A membrane application piece is removed from its container, which may be, for example, a compact, envelope, foil packet or the like. Application to the skin can be achieved in either of two ways, each of which requires a light wetting of the membrane to achieve adhesion to the skin. The skin can either be wet lightly with ordinary water or wetting solution and the membrane applied to the prewetted area; alternately, the user can wet the membrane slightly, enough to give adhesion but not to dissolve it, on her finger or in the palm of her hand, and then place the damp patch on the skin surface to be treated. Once the membrane is in place, the user applies additional water or wetting solution to the membrane, sufficient to return it back to its original dissolvable gel form. The gel can then be rubbed completely into the skin, or left in place for a time, then rubbed in.

The membrane prepared as described above has a number of uses. Without any additional components, the membrane can be applied to the skin and rewetted, and the dissolved membrane on the skin can serve to temporarily stretch, smooth, tighten and remoisturize skin, particularly skin with fine lines and wrinkles. However, the greatest advantage of the membrane is in the delivery of active materials to the skin. Thus, it is particularly preferred that the membrane incorporate one or more active ingredients, either cosmetic or pharmaceutical, either water-soluble or oil-soluble, having a specific beneficial effect on the skin. The membrane serves as an excellent delivery system for a variety of actives, especially for those actives which have particular benefit in spot applications to affected areas. One particular example is the use of the membrane for the application of anti-acne actives. For this purpose, anti-acne compounds, such as salicylic acid or benzoyl peroxide, are incorporated into the gel in the amounts known to be effective for acne treatment, the membrane thus prepared can then be cut to provide, for example, small discs that can be applied directly to a blemish. An additional example is for the application of agents for the treatment of the symptoms of chrono-or photoaging, which thus can be applied selectively to those regions of the skin in need of treatment, for example, at the corner of the eyes or along the upper lip. Actives usefull for this purpose include but are not limited to alpha and beta hydroxyacids, retinoids, soluble collagen, or collagen-stimulating compounds such as Vitamin C or derivatives thereof, Vitamin E and derivatives thereof N-acetyl cysteine, elastin, whey protein, colostrum, N-acetyl D-glucosamine, luteolin, or antioxidants such as green tea and active fractions thereof(EGCG/ECG). Whitening agents, such as kojic acid, licorice extracts, ascorbyl phosphates, ascorbyl glucosides, ascorbic acid or arbutin, can be incorporated to permit localized treatment of age spots, freckles, and skin discolorations associated with hormonal changes. Skin conditioning agents, e.g., compounds that moisturize the skin, or enhance the skin's natural lipid barrier, such as ceramides, cholesterol sulfate, fatty acids, white birch extract, and sclareolide, can also be applied to areas in need by this method. Enzymes having utility in or on the skin, for example, proteases, lipases, cerebrosidases, or melanases, can be incorporated into the membrane. The membranes can also be used to deliver hormones, such as estrogen, progesterone, or DHEA. In the case of inclusion of one or more actives in the membrane, the active(s) will be incorporated in an amount sufficient to deliver the known effective dosage for that particular active.

The foregoing examples are provided as specific illustrations only; those skilled in the art will immediately recognize the scope of utility of the present delivery system. It can be used to deliver virtually any cosmetic or pharmaceutical ingredient, active or otherwise, that has an effect when delivered topically. Further examples of therapeutic actives include but are not limited to analgesics, anesthetics, antibacterials, antiyeast agents, antifungal agents, antiviral agents, antidermatitis agents, antipruritic agents, antiemetics, anti-motion sickness agents, antiirritant agents, anti-inflammatory agents, antihyperkeratolytic agents, anti-dry skin agents, antiperspirants, antipsoriatic agents, antiseborrheic agents, antiaging agents, antiasthmatic agents and bronchodilators, sunscreen agents, antihistamine agents, wound-healing agents, vitamins, corticosteroids, or tanning agents.

The membrane delivery system, as described above, has a number of advantages over traditional vehicles used for delivery of actives to the skin, as well as over other types of patches. The application pieces are convenient to use and easier to carry and store than bottles and jars of lotions and creams. Like other patch-type products, the membrane of the invention can remain on the skin for prolonged periods, and therefore does permit sustained delivery of active ingredients to the skin; however, unlike other skin patches and films, the rewetted membrane does not have to be peeled or washed off after use, but simply dissolves and is rubbed into the skin, and in fact can provide immediate benefits by the rubbing in of the gel right after application and wetting, thereby avoiding the potentially unattractive appearance of a patch in a highly visible location such as the face. These advantages alone make the membrane a superior product. An additional advantage can be found, however, in the fact that the membrane also serves as a stabilizer for the active ingredients. Because the application pieces are maintained in a dry state until use, active ingredients that are normally adversely affected by the presence of water, or other environmental factors, e.g., retinoids, green tea polyphenols, enzymes, or Vitamin C, substantially retain their activity even after prolonged periods of storage. Normally compounds such as these have to be specially formulated or delivered in special packaging in order to retain their activity before the product reaches the consumer. It is quite unexpected that such labile actives can be rendered stable in so simple and relatively inexpensive a manner. In some cases, however, it may be desirable to provide particularly labile actives in encapsulated form to further stabilize their activity.

EXAMPLES

Example 1

This example illustrates the preparation of a membrane of the present invention.

A slurry of sodium alginate, 10% by weight in water, is prepared. To the slurry is added 1% by weight of hyaluronic acid, 2% salicylic acid and 1% collagen, as film-forming agent, and the combined ingredients are mixed thoroughly.

To the slurry is added 3% by weight of calcium chloride, to cross link the alginate. The resulting gel is freeze dried in blocks under standard freeze-drying conditions, and then is sliced to a thickness of 0.5 mm, and cut to form wafers.

To prepare a wetting solution, malic acid is added to water in an amount of 2% by weight.

For use of the wafer as an anti-blemish product, the user lightly wets the area of skin containing the blemish to be treated. The wafer is then pressed onto the damp skin, and wetting solution is applied to the wafer. A gentle rubbing of the wetted wafer shortly initiates dissolution of the membrane into a gel, and the gel vehicle is further rubbed in, so as to deliver the salicylic acid to the blemish, leaving virtually no trace of the original wafer on the skin.

Example 2

This example illustrates the composition of a dry membrane of the invention.

| Material | Weight (grams/100 grams) |
| --- | --- |
| Sodium alginate | 48 |
| Cellulose gum | 19 |
| Squalane | 11 |
| Rayon | 9 |
| PPG-15-stearyl ether | 4.5 |
| Hyaluronic acid | 5 |
| Potassium carbonate | 0.5 |
| PEG-40 sorbitan peroleate | 2 |
| Soluble collagen | 1 |

What we claim is:

1. A delivery system for topical application to the skin comprising a freeze-dried, partially cross-linked polymeric gel membrane which can be reversibly returned to a dissolvable gel form upon the application of a wetting agent in which the membrane comprises a crosslinkable polymer and a disrupting agent, in which the disrupting agent is hyaluronic acid.

2. The system of claim 1 in which the polymer is selected from the group consisting of alginates, collagen, and starches.

3. The system of claim 2 in which the polymer is an alginate.

4. The system of claim 1 which comprises a biologically active agent.

5. The system of claim 4 in which the biologically active agent is selected from the group consisting of alpha hydroxy acids, beta hydroxy acids, benzoyl peroxide, retinoids, antioxidants, collagen, collagen-stimulating agents, N-acetyl cysteine, elastin, whey protein, whitening agents, skin conditioning agents, enzymes, and hormones.

6. A delivery system for topical application to the skin comprising a freeze-dried, partially cross-linked polymeric gel membrane which can be reversibly returned to a dissolvable gel form upon the application of a wetting agent, the membrane also comprising a biologically active agent, in which the biologically active agent is salicylic acid.

7. A delivery system for topical application of a biologically active agent to the skin comprising a freeze-dried, partially cross-linked polymeric gel membrane, the membrane comprising a crosslinkable polymer selected from the group consisting of alginates, starches, and collagen; a crosslinking disrupting agent selected from the group consisting of breakdown products and derivatives of chitin and mucopolysaccharides; and a biologically active agent, in which the biologically active agent is salicylic acid.

8. The system of claim 7 in which the polymer is an alginate and the disrupting agent is selected from the group consisting of chitosan; hyaluronic acid; glucuronic acid; oligosaccharides comprising glucosamine, galactosamine, and/or mannosamine monomeric units; hygroscopic water soluble amino acids or peptides composed thereof; and glycerin and glycerin derivatives.

9. The system of claim 8 in which the disrupting agent is hyaluronic acid.

10. The system of claim 8 which also comprises a water-soluble film-forming agent.

11. A delivery system for topical application of a biologically active agent to the skin comprising a freeze-dried, partially cross-linked polymeric gel membrane, the membrane comprising a crosslinkable polymer selected from the group consisting of alginates, starches, and collagen; a crosslinking disrupting agent selected from the group consisting of breakdown products and derivatives of chitin and mucopolysaccharides; and a biologically active agent which is an antioxidant, in which the antioxidant is a green tea polyphenol.

12. The system of claim 11 in which the polymer is an alginate and the disrupting agent is selected from the group consisting of chitosan; hyaluronic acid; glucuronic acid; oligosaccharides comprising glucosamine, galactosamine, and/or mannosamine monomeric units; hygroscopic, water soluble amino acids or peptides composed thereof; and glycerin and glycerin derivatives.

13. The system of claim 11 in which the disrupting agent is hyaluronic acid.

14. The system of claim 11 which also comprises a water-soluble film-forming agent.

15. A method of delivering a biologically active agent to the skin which comprises applying to the skin the delivery system comprising a freeze-dried, partially cross-linked polymeric gel membrane which can be reversibly returned to a dissolvable gel form upon the application of a wetting agent and the biologically active agent, wetting the, membrane with a wetting agent, whereby upon wetting, the membrane reverts to a dissolvable gel form, in which the wetting agent comprises at least one cosmetically acceptable acid.

16. The method of claim 15 in which the acid is an alpha or beta hydroxy acid.

17. The method of claim 15 in which the membrane comprises a crosslinkable polymer selected from the group consisting of alginates, starches and collagen, and a crosslinking disrupting agent selected from the group consisting of breakdown products and derivatives of chitin or mucopolysaccharides.

18. The method of claim 17 in which the disrupting agent is hyaluronic acid.

19. The method of claim 15 in which at least one of the membrane or wetting solution comprises an acid, and the other comprises a bicarbonate.

20. A kit for delivery of a biologically active agent to the skin, the kit comprising at least one freeze-dried, partially cross-linked polymeric gel membrane which reverts to a dissolvable gel form upon the application of a wetting agent; and a wetting agent therefor.

21. The kit of claim 20 in which the membrane comprises a crosslinkable polymer selected from the group consisting of alginates, starches, and collagen; a crosslinking disrupting agent selected from the group consisting of breakdown products and derivatives of chitin and mucopolysaccharides; and a biologically active agent.

22. The kit of claim 21 in which the polymer is an alginate, and the disrupting agent is hyaluronic acid.

23. The kit of claim 22 in which the wetting agent contains an acid.

24. The kit of claim 22 in which the membrane contains an acid, and the wetting agent contains a bicarbonate.

25. The kit of claim 22 in which the wetting agent contains an acid, and the membrane contains a bicarbonate.

26. The kit of claim 21 in which the membrane comprises an alginate polymer and the disrupting agent is hyaluronic acid, the wetting agent comprises an acid, and the biologically active agent is selected from the group consisting of alpha hydroxy acids, beta hydroxy acids, benzoyl peroxide, retinoids, antioxidants, collagen, collagen-stimulating agents, N-acetyl cysteine, elastin, whey protein, whitening agents, skin conditioning agents and hormones.

* * * * *